(12) United States Patent
Steiger et al.

(10) Patent No.: US 9,975,908 B2
(45) Date of Patent: May 22, 2018

(54) METAL OXIDE PRECURSORS, COATING COMPOSITIONS CONTAINING SAME, AND USE THEREOF

(71) Applicant: Evonik Degussa GmbH, Essen (DE)

(72) Inventors: Jurgen Steiger, Taipei (TW); Duy Vu Pham, Oberhausen (DE); Alexey Merkulov, Recklinghausen (DE); Dennis Weber, Dortmund (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days. days.

(21) Appl. No.: 14/900,890

(22) PCT Filed: Jun. 6, 2014

(86) PCT No.: PCT/EP2014/061804
§ 371 (c)(1),
(2) Date: Dec. 22, 2015

(87) PCT Pub. No.: WO2014/206709
PCT Pub. Date: Dec. 31, 2014

(65) Prior Publication Data
US 2016/0137671 A1     May 19, 2016

(30) Foreign Application Priority Data
Jun. 25, 2013 (DE) .......................... 10 2013 212 018

(51) Int. Cl.
| | | |
|---|---|---|
| G03F 7/00 | (2006.01) | |
| C07F 5/00 | (2006.01) | |
| C23C 18/06 | (2006.01) | |
| C23C 18/12 | (2006.01) | |
| C23C 18/14 | (2006.01) | |
| C23C 18/02 | (2006.01) | |
| G03F 7/028 | (2006.01) | |
| G03F 7/029 | (2006.01) | |

(52) U.S. Cl.
CPC ................ *C07F 5/00* (2013.01); *C23C 18/02* (2013.01); *C23C 18/06* (2013.01); *C23C 18/1216* (2013.01); *C23C 18/14* (2013.01); *G03F 7/028* (2013.01); *G03F 7/029* (2013.01)

(58) Field of Classification Search
CPC ....................................................... C07F 5/00
See application file for complete search history.

(56) References Cited

U.S. PATENT DOCUMENTS

| | | |
|---|---|---|
| 8,546,594 B2 | 10/2013 | Steiger et al. |
| 8,580,989 B2 | 11/2013 | Steiger et al. |
| 8,841,164 B2 | 9/2014 | Steiger et al. |
| 8,859,332 B2 | 10/2014 | Steiger et al. |
| 8,889,476 B2 | 11/2014 | Thiem et al. |
| 9,059,299 B2 | 6/2015 | Steiger et al. |
| 9,115,422 B2 | 8/2015 | Steiger et al. |
| 9,194,046 B2 | 11/2015 | Hoppe et al. |
| 2009/0212280 A1* | 8/2009 | Werner ................. C09K 11/06 257/40 |
| 2009/0252772 A1* | 10/2009 | Henglein ............ C09B 67/0098 424/401 |
| 2010/0210069 A1 | 8/2010 | Seon et al. |
| 2012/0202318 A1* | 8/2012 | Steiger ................ C23C 18/1216 438/104 |
| 2013/0011630 A1* | 1/2013 | Sullivan ................. C08G 77/58 428/195.1 |
| 2013/0059414 A1 | 3/2013 | Kim et al. |
| 2013/0116463 A1* | 5/2013 | Steiger ................... C07F 5/069 556/1 |
| 2015/0053966 A1* | 2/2015 | Steiger ............. H01L 21/02472 257/43 |

FOREIGN PATENT DOCUMENTS

| | | |
|---|---|---|
| DE | 10 2010 031 592 A1 | 1/2012 |
| WO | WO 2007/024461 A2 | 3/2007 |

OTHER PUBLICATIONS

International Search Report dated Oct. 27, 2014 in PCT/EP2014/061804.
U.S. Appl. No. 13/390,840, filed Jul. 2012, US 2012/0181488 A1, Steiger, et al.
U.S. Appl. No. 13/809,423, filed May 2013, US 2013/0104773 A1, Steiger, et al.
U.S. Appl. No. 14/395,339, filed Mar. 2015, US 2015/0076421 A1, Steiger, et al.
U.S. Appl. No. 14/407,681, filed Jun. 2015, US 2015/0170913 A1, Steiger, et al.

\* cited by examiner

*Primary Examiner* — Chanceity Robinson
(74) *Attorney, Agent, or Firm* — Grüneberg and Myers, PLLC

(57) ABSTRACT

The present invention relates to metal oxide precursors comprising i) at least one metal atom selected from the group consisting of In, Ga, Zn and Sn, ii) at least one non-photocrosslinkable ligand and iii) at least one photocrosslinkable ligand, to liquid coating compositions comprising the precursors, and to their use.

8 Claims, No Drawings

METAL OXIDE PRECURSORS, COATING COMPOSITIONS CONTAINING SAME, AND USE THEREOF

This application is a National Stage of PCT/EP2014/061804, which was filed on Jun. 6, 2014. This application is based upon and claims the benefit of priority of German Application No. 102013212018.4, which was filed on Jun. 26, 2013.

The invention relates to metal oxide precursors, to liquid coating compositions comprising them, and to their use.

Metal-oxidic layers are essential to numerous applications, particularly within the sector of semiconductor technology. Metal-oxidic layers can be applied by diverse methods to a variety of surfaces. These methods include vacuum methods (sputtering, chemical vapour deposition) and wet-chemical methods. Of these, the wet-chemical methods, also referred to as liquid-phase methods, have the advantage that they require less, and less complex, apparatus. Liquid-phase methods may be carried out using dispersed nanoparticles or using precursor systems. Dispersed nanoparticles have the disadvantage here that their preparation involves considerable apparatus and that the semiconductor layers produced using them often have adverse properties.

For this reason, preference is often given to liquid-phase coating methods which employ precursors. A metal oxide precursor is a compound which can be decomposed thermally or with electromagnetic radiation and with which layers containing metal oxide can be formed in the presence or absence of oxygen or other oxidants.

A variety of precursors for producing metal oxide layers have been described in the prior art. For instance, WO 2011/020781 A1 discloses liquid-phase methods for producing layers containing indium oxide, where indium oxoalkoxides can be used, which may also have halogen, hydroxyl or hydroxyalkoxy radicals. Similar liquid-phase methods and precursors suitable for producing layers containing indium, gallium, tin, or zinc oxide are also described in WO 2011/020792 A1. WO 2012/010427 A1 discloses halogen-containing indium oxoalkoxides which are likewise suitable for producing layers containing indium oxide and which may have β-hydroxy acid ester groups. WO 2012/010464 A1 additionally discloses likewise halogen-containing indium oxoalkoxides which are suitable for producing layers containing indium oxide and which as well as oxo and alkoxy radicals may also have hydroxyl groups. The above-stated precursors share an unsuitability for direct structuring with UV light. Structured layers, which are of interest for diverse applications in the semiconductor industry, can be produced with these precursors only with the attendant use of photoresists, with the consequences of increased consumption of materials, a multiplicity of additional operating steps, and an additional stress on the oxide layer as a result of contact with aggressive materials.

However, precursors suitable for direct production of structured coatings (e.g. via local converting by exposure to electromagnetic radiation through a corresponding mask), having exclusively photocrosslinkable ligands, also have disadvantages. For instance, US 2010/0210069 A1 and US 2010/0258793 A1, in addition to precursors suitable for the production of semiconductor layers, disclose zinc precursors and indium precursors, respectively, which may have hydroxides, alkoxides or else photocrosslinkable (meth) acrylate radicals. Precursors with exclusively photocrosslinkable ligands, however, have the disadvantage that they must be converted at a relatively high temperature, and the resultant layers often have relatively poor electronic properties. Furthermore, they are poorly soluble in common solvents.

It is an object of the present invention, therefore, to provide metal oxide precursors which overcome the disadvantages of the prior art and which are suitable in particular for production of coating compositions for liquid-phase methods.

This object is presently solved by the metal oxide precursor of the invention, comprising
i) at least one metal atom selected from the group consisting of In, Ga, Zn and Sn,
ii) at least one non-photocrosslinkable ligand and
iii) at least one photocrosslinkable ligand.

A "metal atom" for the purposes of the present invention refers both to a metal atom and to a semi-metal atom. The same applies in respect of the "metal oxides", and "metal oxide-containing layers" which can be produced using them. In addition to achieving the object set in accordance with the invention, the metal oxide precursors of the invention have the advantage, moreover, that they display significantly improved solubility in a variety of solvents and can be converted into metal oxide-containing layers at particularly low temperatures. The metal oxide layers which can be produced using them also have particularly good electrical properties.

Non-photocrosslinkable ligands of the metal oxide precursor are ligands which undergo no change on exposure to electromagnetic radiation, more particularly to UV light. Preferred non-photocrosslinkable ligands may be selected from the group of radicals consisting of oxo radicals, hydroxyl radicals, alkoxy radicals, nitrate radicals and halide radicals.

Also particularly suitable for generating metal oxide-containing layers are oxo radicals, hydroxyl radicals and alkoxy radicals. Precursors particularly well suited to the production of metal oxide-containing layers have at least one oxo radical and at least one alkoxy radical.

One particularly well-suited metal oxide precursor has, as non-photocrosslinkable ligands, exclusively oxo radicals, alkoxy radicals and radicals selected from the group consisting of nitrate radicals and halide radicals.

A photocrosslinkable ligand in the present context is a radical which as a result of exposure to electromagnetic radiation, more particularly to UV light, is able to crosslink with a further photocrosslinkable ligand of another precursor. Particularly good metal oxide precursors have, as photocrosslinakble ligands, ligands which are selected from the group of radicals consisting of acrylate radicals, methacrylate radicals and allyl radicals.

Particularly good semiconductor properties are further displayed by layers of metal oxide precursors whose metal atom is indium.

One especially preferred precursor has the generic formula $[In_6(\mu_6\text{-}O)(\mu^2\text{-}OR)_{12-x}Cl_6(R')_x]^{2-}$ with $R=C_{1-10}$ alkyl, R'=acrylate or methacrylate and x=1-10. A $C_{1-10}$ alkyl radical here is an alkyl radical having 1 to 10 carbon atoms.

Another especially preferred precursor has the generic formula $[In_6(\mu_6\text{-}O)(\mu^2\text{-}OR)_{12-x}(NO_3)_6(R')_x]^{2-}$ with $R=C_{1-10}$ alkyl, R'=acrylate or methacrylate and x=1-10. Here again, a $C_{1-10}$ alkyl radical is an alkyl radical having 1 to 10 carbon atoms.

The metal oxide precursors of the invention may be prepared, for example, by addition of compounds containing the photocrosslinkable ligand, more particularly methacrylic acid, acrylic acid and/or allylic acid, to corresponding metal oxide precursors having non-photocrosslinkable ligands, with partial exchange of the ligands.

The present invention further provides a liquid coating composition which has at least one precursor of the above-described kind and at least one solvent.

With further preference it comprises at least one photoinitiator.

With particular preference the photoinitiator is phenylbis (2,4,6-trimethylbenzoyl)phosphine oxide.

The present invention additionally provides for the use of a precursor of the invention or of a coating composition of the invention for producing structured metal-oxidic layers.

The present invention further provides a method for producing structured metal-oxidic layers, using a coating composition of the invention. In this method, the coating composition of the invention is a) applied to a substrate, b) exposed through a mask to electromagnetic radiation, c) optionally heat-treated, d) treated with a developer and e) converted thermally and/or with electromagnetic radiation. The electromagnetic exposure in b) takes place preferably with radiation having a wavelength of λ=300-380 nm. In the case of a heat treatment in step c), only the unexposed regions remain after the development in step d). If no heat treatment step c) is carried out, it is instead the exposed regions which are left. Used preferably as developer in step d) is 1-methoxy-2-propanol. In step e), the layer is converted—that is, there is a conversion to form a metal oxide-containing layer. A thermal conversion in step e) takes place preferably at temperatures greater than 300° C., preferably at 350° C. A conversion with electromagnetic exposure in step e) takes place preferably with significant fractions of radiation in the range of 170-210 nm and of 250-258 nm, more particularly with UV radiation having wavelengths λ=184 nm and 254 nm.

Here, radiation "with significant fractions of radiation in the range of 170-210 nm and of 250-258 nm" means radiation whose intensity, determined for these two wavelength ranges collectively, based on the sample to be exposed, is at least 5 mW/cm$^2$, with the proviso that the weaker of the two ranges in terms of intensity still has an intensity, relative to the substrate, of at least 0.5 mW/cm$^2$. The absolute values can be measured directly and wavelength-dependently using various commercial instruments. An example that may be stated is the Hamamatsu UV Power Meter C9536.

The exposure preferably—since this leads to particularly good electronic properties—takes place with electromagnetic radiation having significant fractions of radiation in the range of 183-187 nm and of 250-258 nm, on the basis again of a corresponding understanding of the term "having significant fractions" (the intensity determined for these two wavelength ranges collectively, based on the sample to be exposed, is at least 5 mW/cm$^2$, with the proviso that the weaker of the two ranges in terms of intensity still has an intensity, based on the substrate, of at least 0.5 mW/cm$^2$.

Particularly good results are achieved, furthermore, if the radiation having significant fractions of radiation in the range of 170-210 nm and of 250-258 nm, more preferably such radiation having significant fractions in the range of 183-187 nm and of 250-258 nm, in an intensity/wavelength spectrum scaled in each case linearly in relation to the two axes, over the entire emission of the lamp, exhibits at least 85% of its intensity (determined via the percentage fraction of the sum of the integrals of the sub-ranges, as a proportion of the overall radiation intensity determined as an integral over all the wavelengths of the spectrum) within the two ranges identified in each case.

Corresponding radiation having significant fractions of radiation in the range of 170-210 nm and of 250-258 nm may be generated preferably by using low-pressure mercury vapour lamps, more particularly low-pressure quartz-glass mercury vapour lamps. One low-pressure quartz-glass mercury vapour lamp which can be used with particular preference is a lamp which is equipped with the GLF-100 illuminant and is available under the trade name Model 144AX-220 from Jelight Company, Inc.

Without having any restricting effect themselves, the examples which follow are intended to elucidate in more detail the subject matter of the present invention.

The layers produced with the precursors of the invention are suitable advantageously for the production of conducting, semiconductor or dielectric layers, for example in TFTs or solar cells. TFTs can be used advantageously for the active driving of pixels in LCDs. Another application is that of switching circuits composed of TFTs, for the purpose of realizing RFID tags, for example.

EXAMPLE 1

Synthesis of $[In_6(\mu_6\text{-}O)(\mu^2\text{-}OR)_{12-x}Cl_6(R')_x]^{2-}$ with R'=Methacrylate 50 mg $[In_6(\mu_6\text{-}O)(\mu_2\text{-}OMe)_{12}Cl_6]^{2-}[NH_2Me_2]^{2+}$ were dissolved in 1 mL of 1-methoxy-2-propanol (anhydrous). Then 26 mg of methacrylic acid were added and the mixture was stirred at room temperature for 10 minutes. The resulting mixture was centrifuged, and the centrifugate was evaporated down and dried.

Production of the Coating Composition

The solid obtained was dissolved in 1-methoxy-2-propanol, to give a solution having a concentration of 100 mg/mL in respect of the precursor. As photoinitiator, 8% by weight of Irgacure 819 (phenylbis(2,4,6-trimethylbenzoyl)phosphine oxide) was added. This solution was subsequently diluted in a volume ratio of 1:2 with 1-methoxy-2-propanol.

Production of Structured Layers

The solution was applied to a substrate by spincoating and subsequently exposed with UV light with a wavelength λ=365 nm, selectively by means of a mask, on a mask aligner. In the course of the subsequent development, the unexposed portions were removed with a developer (1-methoxy-2-propanol). This left the unexposed portions. The structures obtained were converted by means of a UVO treatment with radiation of wavelength λ=184 nm and 254 nm and thermal reaction at 350° C. into structures containing indium oxide.

EXAMPLE 2

Synthesis of $[In_6(\mu_6\text{-}O)(\mu^2\text{-}OR)_{12-x}(NO_3)_6(R')_x]^{2-}$ with R'=Methacrylate 50 mg $[In_6(\mu_6\text{-}O)(\mu_2\text{-}OMe)_{12}(NO_3)_6]^{2-}[NH_2Me_2]^{2+}$ (MeOH)$_2$ were dissolved in 1 mL of 1-methoxy-2-propanol (anhydrous). Then 26 mg of methacrylic acid were added and the mixture was stirred at room temperature for 10 minutes. The resulting mixture was centrifuged, and the centrifugate was evaporated down and dried.

Production of the Coating Composition

The solid obtained was dissolved in 1-methoxy-2-propanol, to give a solution having a concentration of 100 mg/mL in respect of the precursor. As photoinitiator, 8% by weight of Irgacure 819 (phenylbis(2,4,6-trimethylbenzoyl)phosphine oxide) was added. This solution was subsequently diluted in a volume ratio of 1:2 with 1-methoxy-2-propanol.

Production of Structured Layers

The solution was applied to a substrate by spincoating and subsequently exposed with UV light with a wavelength λ=365 nm, selectively by means of a mask, on a mask aligner. In the course of the subsequent development, the unexposed portions were removed with a developer (1-methoxy-2-propanol). This left the unexposed portions. The structures obtained were converted by means of a UVO treatment with radiation of wavelength λ=184 nm and 254 nm and thermal reaction at 350° C. into structures containing indium oxide.

COMPARATIVE EXAMPLES

Synthesis of a precursor with exclusively Photocrosslinkable Groups

A solution was made from 25 mg of In(III) isopropoxide (manufacturer: Alfa Aesar) per 1 mL of methacrylic acid. The mixture was boiled under reflux at 100° C. for 1 hour. The resulting mixture was centrifuged, and the centrifugate was evaporated down and dried. NMR measurements show exclusively methacrylate groups, i.e. photocrosslinkable ligands.

Production of the Coating Composition

The residue obtained was dissolved in 1-methoxy-2-propanol, to give a solution having a concentration of 33 mg/mL in respect of the precursor. As photoinitiator, 8% by weight of Irgacure 819 (phenylbis(2,4,6-trimethylbenzoyl)phosphine oxide) was added.

Production of Structured Layers

The solution was applied to a substrate by spincoating and subsequently exposed with UV light with a wavelength λ=365 nm, selectively by means of a mask, on a mask aligner. In the course of the subsequent development, the unexposed portions were removed with a developer (1-methoxy-2-propanol). This left the unexposed portions. The structures obtained were converted by means of a UVO treatment with radiation of wavelength λ=184 nm and 254 nm and thermal reaction at 350° C. and 550° C., respectively, into structures containing indium oxide.

In both examples the layers were produced by spincoating with the following parameters: 100 µl of coating composition were applied at 3000 rpm over 30 seconds to a silicon wafer having an SiO$_2$ layer thickness of 230 nm and pre-structured source and drain contacts made from ITO. Thermal conversion took place on a hotplate.

Electrical characterization was carried out in both cases with a Keithley 2612 System source meter with Keithley 3706-NFP System switch/multimeter. The samples were measured at room temperature under an N$_2$ atmosphere. Characterization was carried out after the temperature treatment. The (pre-structured) gate, source and drain contacts here were connected to the apparatus via tungsten measurement tips. A voltage profile between gate electrode and source electrode between −20 and +30 V was run, and the current which flowed between source electrode and drain electrode was recorded. This data can be used to calculate the mobility values as follows:

$$\mu_{lin} = \frac{\partial I_D}{\partial V_G} \frac{L}{WC_i V_D}$$

$$\mu_{sat} = \frac{2L}{WC_i} \left( \frac{\partial (\sqrt{I_D})}{\partial V_G} \right)^2$$

where $I_D$ and $V_G$ are the current between drain and source and the voltage applied at the gate, respectively. L and W correspond to the length and width of the channel, and $C_i$ is the dielectric constant of the dielectric. The higher the mobility value, the better the material.

Further characteristic properties are the switch-on voltage ($V_{ON}$), which describes the point at which current flow between source electrode and drain electrode begins; this value ought to be very close to 0 V. $I_{ON}$ is the maximum current flow between source electrode and drain electrode (measured here with a gate voltage of 30 V); this value ought to be very high. The ratio ($I_{ON}/I_{OFF}$) describes the ratio between $I_{ON}$ and the current flow in the switched-off state (below $V_{ON}$); this value ought to be very high.

The table set out below summarizes the electrical characterization data.

TABLE

| Material | $T_{anneal}$ [° C.] | $V_{On}$ [V] | $I_{On}$ [mA] | $I_{On}/I_{Off}$ | $\mu_{lin}$ [cm$^2$/Vs] | $\mu_{sat}$ [cm$^2$/Vs] |
|---|---|---|---|---|---|---|
| Hybrid ligand Ex. 1 | 350 | −0.5 | 0.55 | 6 × 10$^6$ | 3.08 | 1.12 |
| Hybrid ligand Ex. 2 | 350 | 0.5 | 0.4 | 6 × 10$^6$ | 2.24 | 0.82 |
| Methacrylate | 350 | 4 | 2.8 × 10$^{-3}$ | 1.6 × 10$^4$ | 0.013 | 0.014 |

The invention claimed is:

1. A liquid coating composition, comprising
at least one metal oxide precursor, which is a coordination complex comprising:
i) at least one metal atom selected from the group consisting of In, Ga, Zn and Sn;
ii) at least one non-photocrosslinkable ligand; and
iii) at least one photocrosslinkable ligand
wherein the at least one photocrosslinkable ligand is selected from the group consisting of an acrylate, a methacrylate and an allyl;
at least one solvent; and
at least one photoinitiator.

2. The liquid coating composition according to claim 1, wherein the at least one non-photocrosslinkable ligand is selected from the group consisting of an oxo radical, a hydroxyl radical, an alkoxy radical, a nitrate radical and a halide radical.

3. The liquid coating composition according to claim 2, comprising, as at least one non-photocrosslinkable ligand, at least one oxo radical and at least one alkoxy radical.

4. The liquid coating composition according to claim 1, comprising, as the at least one non-photocrosslinkable ligand, an oxo, an alkoxy and at least one selected from the group consisting of a nitrate and a halide.

5. The liquid coating composition according to claim 1, wherein the at least one metal atom is In.

6. A metal oxide precursor having formula:

wherein:

R represents a $C_{1-10}$ alkyl,

R' represents acrylate or methacrylate, and x represents 1-10.

7. A metal oxide precursor having formula:

$$[In_6(\mu_6\text{-}O)(\mu^2\text{-}OR)_{12-x}(NO_3)_6(R')_x]^{2-}$$

wherein:

R represents a $C_{1-10}$ alkyl,

R' represents acrylate or methacrylate, and x represents 1-10.

8. The liquid coating composition according to claim 1, comprising phenylbis(2,4,6-trimethyl benzoyl)phosphine oxide as the photoinitiator.

* * * * *